US008585965B2

(12) United States Patent
Comolli et al.

(10) Patent No.: US 8,585,965 B2
(45) Date of Patent: *Nov. 19, 2013

(54) STERILIZATION OF POLYMERIC MATERIALS

(71) Applicant: Ethicon, Inc., Sommerville, NJ (US)

(72) Inventors: James Comolli, Boxborough, MA (US); Stephen C. Yeadon, Hampton, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/685,367

(22) Filed: Nov. 26, 2012

(65) Prior Publication Data
US 2013/0084381 A1   Apr. 4, 2013

Related U.S. Application Data

(63) Continuation of application No. 11/555,016, filed on Oct. 31, 2006.

(51) Int. Cl.
A61L 2/00 (2006.01)

(52) U.S. Cl.
USPC .............................................. 422/22; 422/24

(58) Field of Classification Search
USPC ........................................................ 422/22, 24
See application file for complete search history.

(56) References Cited

U.S. PATENT DOCUMENTS

| 3,537,967 | A | 11/1970 | Kelly et al. |
| 5,258,423 | A | 11/1993 | Crabb et al. |
| 5,342,752 | A | 8/1994 | Platz et al. |
| 5,362,442 | A | 11/1994 | Kent |
| 5,688,900 | A | 11/1997 | Cooper et al. |
| 6,051,648 | A | 4/2000 | Rhee et al. |
| 6,171,549 | B1 | 1/2001 | Kent |
| 6,187,572 | B1 | 2/2001 | Platz et al. |
| 6,214,534 | B1 | 4/2001 | Horowitz et al. |
| 6,239,048 | B1 | 5/2001 | Wilson et al. |
| 6,277,337 | B1 | 8/2001 | Goodrich, Jr. et al. |
| 6,346,216 | B1 | 2/2002 | Kent |
| 6,514,515 | B1 | 2/2003 | Williams |
| 6,548,242 | B2 | 4/2003 | Horowitz et al. |
| 6,635,222 | B2 | 10/2003 | Kent |
| 6,696,060 | B2 | 2/2004 | Grieb et al. |
| 6,746,661 | B2 | 6/2004 | Kaplan |
| 6,875,400 | B2 | 4/2005 | Speer et al. |

(Continued)

FOREIGN PATENT DOCUMENTS

| GB | 2344519 A | 6/2000 |
| JP | 2002-020205 A | 1/2002 |

(Continued)

OTHER PUBLICATIONS

Mark Wainwright, "Pathogen Inactivation in Blood Products"; Current Medicinal Chemistry 9, pp. 127-143; (2002).

(Continued)

Primary Examiner — Kevin Joyner
(74) Attorney, Agent, or Firm — David R. Crichton

(57) ABSTRACT

A method of sterilizing a polymeric material that is sensitive to radiation. The method includes the steps of applying at least one radiosensitizer to the polymeric material and irradiating the polymeric material with a suitable radiation at an effective dose and time to sterilize the polymeric material. Also disclosed is a method of enhancing the ability of a medical device to withstand sterilization by radiation and a bioabsorbable polymeric medical device.

8 Claims, 4 Drawing Sheets

(56) References Cited

U.S. PATENT DOCUMENTS

| | | |
|---|---|---|
| 6,908,591 B2 | 6/2005 | MacPhee et al. |
| 2002/0142168 A1 | 10/2002 | Speer et al. |
| 2003/0012687 A1 | 1/2003 | Macphee et al. |
| 2003/0073650 A1 | 4/2003 | Reddy et al. |
| 2003/0143106 A1 | 7/2003 | Kent et al. |
| 2003/0143256 A1 | 7/2003 | Gen |
| 2003/0213920 A1 | 11/2003 | Miekka et al. |
| 2004/0091388 A1 | 5/2004 | MacPhee et al. |

FOREIGN PATENT DOCUMENTS

| | | |
|---|---|---|
| JP | 2003-527210 A | 9/2003 |
| JP | 2004-350935 A | 12/2004 |
| WO | 93/00815 A1 | 1/1993 |
| WO | 9428120 A1 | 12/1994 |
| WO | 9503071 A1 | 2/1995 |
| WO | 9608965 A1 | 3/1996 |
| WO | 0170279 A1 | 9/2001 |
| WO | 02/02110 A1 | 1/2002 |
| WO | 02/051705 A2 | 7/2002 |
| WO | 02096471 A2 | 12/2002 |
| WO | 03020324 A2 | 3/2003 |
| WO | 03020325 A2 | 3/2003 |
| WO | 03026703 A1 | 4/2003 |
| WO | 03026704 A1 | 4/2003 |
| WO | 03026705 A1 | 4/2003 |
| WO | 03026769 A2 | 4/2003 |
| WO | 03103029 A1 | 12/2003 |
| WO | 2005/030137 A2 | 4/2005 |
| WO | 2005/049101 A1 | 6/2005 |

OTHER PUBLICATIONS

Mark Wainwright, "The Emerging Chemistry of Blood Product Disinfection"; The Royal Society of Chemistry, pp. 128-136 (2002).

Joyce M. Hansen and Harry L. Shaffer, "Sterilization and Preservation by Radiation Sterilization"; The British Library—"The World's Knowledge", pp. 729-746.

Phillips, T. L., Radiation Sensitizers and Protectors, Newer Methods of Cancer Treatment, DeVita, Section 3, pp. 2256-2271.

STERILIZATION OF POLYMERIC MATERIALS

This application is a continuation of co-pending U.S. application Ser. No. 11/555,016, filed on Oct. 31, 2006, the entire contents of which are hereby incorporated by reference and for which priority is claimed under 35 U.S.C. §120.

FIELD

This invention relates to polymers and, more particularly, to methods for the sterilization of radiosensitive polymeric materials for the reduction of active biological contaminants.

BACKGROUND

Medical devices designed for implantation are often composed of materials that are gradually broken down by the body into products that are excreted or metabolized. Devices produced from these bioabsorbable materials tend to be more sensitive to certain physical and chemical treatments, including those necessary to sterilize medical devices. In particular, the mechanical integrity of medical devices produced from bioabsorbable polymers frequently suffers when sterilized using conventional irradiation techniques.

Ionizing radiation treatments such as gamma-irradiation, electron beam irradiation, and x-ray irradiation generate free radicals and other activated molecules that damage the biological components of contaminating bacteria, fungi, and viruses and thus ensures their inactivation. However, the constituent atoms of bioabsorbable materials are also damaged by free radicals and activated molecules, which reduces the structural integrity of the material.

Compounding the sterilization issue is the fact that steam sterilization is incompatible with thermally or hydrolytically labile polymers. Ethylene oxide, a common and widely used sterilant, often reacts with such polymers, while also requiring prolonged periods of outgassing.

In view of these issues, many new medical advances cannot be implemented because the sterilization industry is unable to provide a suitable sterilant as part of the manufacturing process. As indicated above, medical devices, such as stents, sutures, catheters and endoscopes, are fabricated from, or coated with, sensitive polymers that cannot tolerate steam, irradiation, or ethylene oxide. Moreover, plasma sterilization has been shown to be incompatible with some medical equipment and leaves toxic residues.

Issues involving sterilization exist in other areas of medical treatment as well, such as blood transfusions, blood factor replacement therapy, organ transplants and other forms of human therapy corrected or treated by intravenous, intramuscular or other forms of injection or introduction. Sterilization is also critical for the various biological materials that are prepared in media which contain various types of plasma and/or plasma derivatives or other biologic materials and which may contain harmful prions, bacteria, viruses and other biological contaminants or pathogens.

U.S. Pat. No. 5,362,442 proposes a method for sterilizing products to remove biological contaminants such as viruses, bacteria, yeasts, molds, mycoplasmas and parasites. The method proposed requires providing the product in a form that contains less than 20% solids and subsequently irradiating the product with gamma irradiation over an extended period of time. The product is irradiated for a period of not less than 10 hours. The extended irradiation time in conjunction with the low level of solids in the product is said to substantially reduce the damage to the product. The method is said to be useful in sterilizing sensitive materials such as blood and blood components.

U.S. Pat. No. 6,187,572 proposes a method for inactivating viral and/or bacterial contamination in blood cellular matter, such as erythrocytes and platelets, or protein fractions. It is proposed that the cells or protein fractions are mixed with chemical sensitizers, frozen or freeze-dried, and irradiated with, for example, UV, visible, gamma or X-ray radiation while in the solid state.

U.S. Pat. No. 6,239,048 proposes a substrate such as a woven or nonwoven fabric bound with a light-activated dye alone or in combination with additional conventional antimicrobial agents. The proposed substrate is impregnated with a light-activated non-leachable dye said to have antimicrobial and/or antiviral characteristics that can be imparted to the substrate. Upon exposure to light, the dye is reported to generate singlet oxygen that is said to kill microorganisms and viruses.

U.S. Pat. No. 6,908,591 proposes methods for sterilizing biological materials to reduce the level of one or more active biological contaminants or pathogens, such as viruses, bacteria, yeasts, molds, fungi, prions or similar agents responsible, for TSEs and/or single or multicellular parasites. The methods proposed involve the use of flavonoid/flavonol stabilizers in sterilizing biological materials with irradiation.

Despite these advances in the art, none of which address the issue of sterilizing polymeric materials, there remains a need for methods of sterilizing such materials that are effective for reducing the level of active biological contaminants or pathogens without an adverse effect on the material.

SUMMARY

In one aspect, provided is a method of sterilizing a polymeric material that is sensitive to radiation, comprising the steps of applying at least one radiosensitizer to the polymeric material and irradiating the polymeric material with a suitable radiation at an effective dose and time to sterilize the polymeric material.

In another aspect, provided is a polymeric medical device, comprising a polymeric composition in the form of a medical device, the medical device having at least a first surface and at least one radiosensitizer applied to the at least first surface of the medical device; wherein the medical device is effective for its intended use following sterilization with radiation.

In yet another aspect, provided is a method of making a polymeric medical device, comprising forming a medical device from a polymeric composition, the medical device having at least a first surface and applying at least one radiosensitizer to the at least first surface of the polymeric medical device; wherein the medical device is effective for its intended use following sterilization with radiation.

In still yet another aspect, provided is a method of producing a article, comprising providing a polymer composition, heating the polymer to a melt processing temperature, forming an article from the polymer composition using a melt processing apparatus, the article having at least a first surface and applying at least one radiosensitizer to the at least first surface of the article, wherein the article is effective for its intended use following sterilization with radiation.

In a further aspect, provided is a method of enhancing the ability of a medical device to withstand sterilization by radiation, comprising the step of applying at least one radiosensitizer to the medical device, wherein the article is effective for its intended use following sterilization with radiation.

BRIEF DESCRIPTION OF THE DRAWINGS

The invention will now be described in more detail with reference to the forms herein disclosed, given only by way of example, and with reference to the accompanying drawings, in which.

DETAILED DESCRIPTION

Definitions

Figure 1:
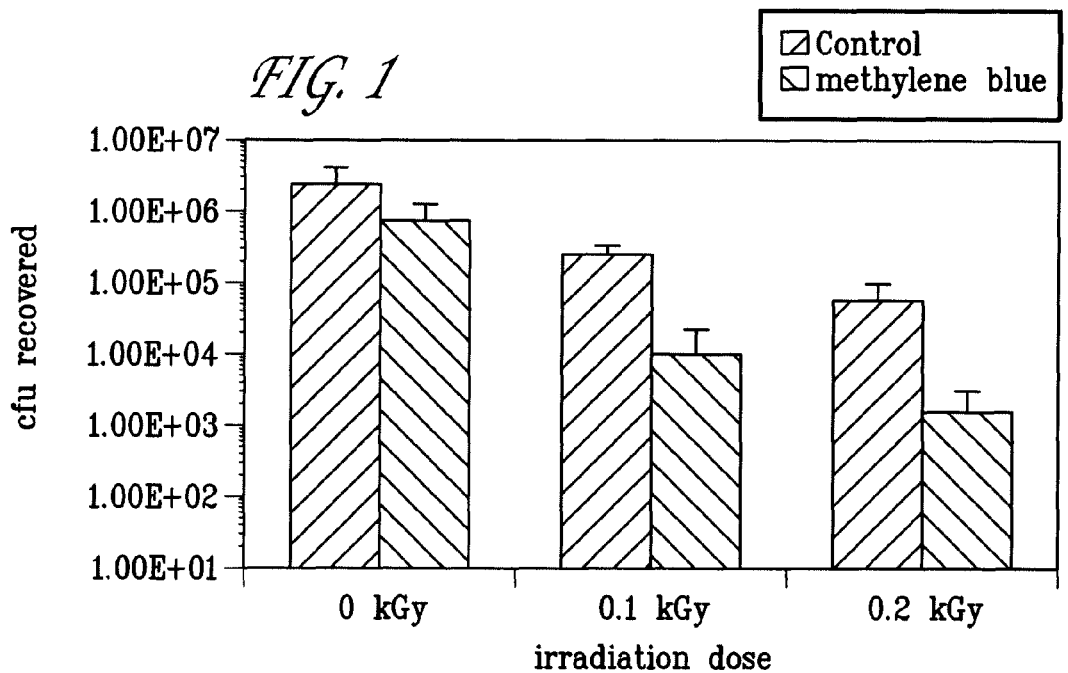
FIG. 1 presents plots of cfu recovered as a function of irradiation dose for the data of Table 2.

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, the term "sterilize" is intended to mean a reduction in the level of at least one active or potentially active biological contaminant or pathogen found on the radiosensitive bioabsorbable materials being treated in accordance herewith.

As used herein, the term "biological contaminant or pathogen" is intended to mean a contaminant or pathogen that, upon direct or indirect contact with a radiosensitive polymeric material, may have a deleterious effect upon a recipient thereof. As used herein, the term "active biological contaminant or pathogen" is intended to mean a biological contaminant or pathogen that is capable of causing a deleterious effect, either alone or in combination with another factor, such as a second biological contaminant or pathogen or a native protein or antibody, upon a recipient of the radiosensitive polymeric material.

As used herein, the term "radiosensitizer" is intended to mean a substance that selectively targets biological contaminants or pathogens, including the various viruses, bacteria (including inter- and intracellular bacteria, such as mycoplasmas, ureaplasmas, nanobacteria, chlamydia, rickettsias), yeasts and molds, rendering them more sensitive to inactivation by radiation, therefore permitting the use of a lower dose of radiation than in the absence of the sensitizer.

As used herein, the term "radiation" is intended to mean radiation of sufficient energy to sterilize at least some component of the irradiated polymeric material. Types of radiation include, but are not limited to, the following: (i) corpuscular (streams of subatomic particles such as neutrons, electrons, and/or protons); (ii) electromagnetic (originating in a varying electromagnetic field, such as radio waves, visible (both mono and polychromatic) and invisible light, infrared, ultraviolet radiation, x-radiation, and gamma rays and mixtures thereof); and (iii) sound and pressure waves. Such radiation is often described as either ionizing (capable of producing ions in irradiated materials) radiation, such as gamma rays, and non-ionizing radiation, such as visible light. The sources of such radiation may vary and, in general, the selection of a specific source of radiation is not critical provided that sufficient radiation is given in an appropriate time and at an appropriate dose to effect sterilization. In practice, gamma radiation is usually produced by isotopes of Cobalt or Cesium, while UV and X-rays are produced by machines that emit UV and X-radiation, respectively, and electrons are often used to sterilize materials in a method known as "E-beam" irradiation that involves their production via a machine. Visible light, both mono- and polychromatic, is produced by machines and may, in practice, be combined with invisible light, such as infrared and UV, that is produced by the same machine or a different machine.

As indicated above, many implanted medical devices are composed of materials that are gradually broken down by the body into products that are excreted or metabolized. Consequently, these "bioabsorbable materials" are more sensitive to the certain physical and chemical treatments, particularly those necessary to sterilize medical devices. This is especially true of exposure of these materials to ionizing radiation such as gamma-irradiation, electron beam irradiation, and x-ray irradiation. Such treatments generate free radicals and other activated molecules that damage the biological components of contaminating bacteria, fungi, and viruses and thus ensures their inactivation. The constituent atoms of bioabsorbable materials are also damaged by free radicals and activated molecules, which reduces the structural integrity of the material.

In one form, a sterilization method that reduces the effective dose of ionizing radiation needed for disinfection of a polymeric material to a level where the structural properties of the material are not significantly affected is disclosed. The method includes the steps of applying at least one radiosensitizer to a polymeric material and irradiating the polymeric material with a suitable radiation at an effective dose to sterilize said polymeric material. The combination of the radiosensitizer with low dose irradiation has been found to enable the effective sterilization of medical devices containing radiosensitive materials.

In another form, provided is a polymeric medical device, comprising: a polymeric composition in the form of a medical device, the medical device having at least a first surface; at least one radiosensitizer applied to the at least first surface of the medical device; wherein the medical device is effective for its intended use following sterilization with radiation.

In yet another form, provided is a method of making a polymeric medical device, comprising: forming a medical device from a polymeric composition, the medical device having at least a first surface; and applying at least one radiosensitizer to the at least first surface of the polymeric medical device; wherein the medical device is effective for its intended use following sterilization with radiation.

In still yet another form, provided is a method of producing a polymeric article, comprising: providing a polymer composition; heating the polymer to a melt processing temperature; forming an article from the polymer composition using a melt processing apparatus, the article having at least a first surface; and applying at least one radiosensitizer to the at least first surface of the polymeric article; wherein the polymeric article is effective for its intended use following sterilization with radiation.

In a further form, provided is a method of enhancing the ability of a polymeric medical device to withstand sterilization by radiation, comprising the step of applying at least one radiosensitizer to the polymeric medical device, wherein the polymeric article is effective for its intended use following sterilization with radiation.

Suitable radiosensitizers include numerous compounds familiar to those skilled in the art including, but not limited to, psoralen and its derivatives and analogs (including 3-carboethoxy psoralens); inactines and their derivatives and analogs; angelicins, khellins and coumarins which contain a halogen substituent and a water solubilization moiety, such as quaternary ammonium ion or phosphonium ion; nucleic acid binding compounds; brominated hematoporphyrin; phthalocyanines; purpurins; porphyrins; halogenated or metal atom-substituted derivatives of dihematoporphyrin esters, hematoporphyrin derivatives, benzoporphyrin derivatives, hydrodibenzoporphyrin dimaleimade, hydrodibenzoporphyrin, dicyano disulfone, tetracarbethoxy hydrodibenzoporphyrin, and tetracarbethoxy hydrodibenzoporphyrin dipropionamide; doxorubicin and daunomycin, which may be modified with halogens or metal atoms; netropsin; BD peptide, S2 peptide; S-303 (ALE compound); dyes, such as hypericin, methylene blue, eosin, fluoresceins (and their derivatives), flavins, merocyanine 540; photoactive compounds, such as bergapten; and SE peptide. As may be appreciated, derivatives of these compounds, particularly halogenated (brominated) entities, can also be used. In one form, incorporation of riboflavin into the coating of the polymeric material polygalactin 910 is contemplated. As may be appreciated by those skilled in the art, polygalactin 910 is used to produce Vicryl® suture material. When methylene blue is selected as the radiosensitizer, an effective amount to be employed will range from about 20 µg/mL to about 75 µg/mL (about 20 ppm to about 75 ppm). When riboflavin is selected as the radiosensitizer, an effective amount to be employed will range from about 200 µg/mL to about 5 mg/mL (about 200 ppm to about 5 ppt).

At least one radiosensitizer may be introduced into a polymeric material according to any of the methods and techniques known and available to one skilled in the art, including, for example, but not by way of limitation, soaking the polymeric material in a solution containing the radiosensitizer(s) at atmospheric pressure and room temperature. Alternatively, the at least one radiosensitizer may be introduced by soaking the polymeric material in a solution containing the radiosensitizer(s) under pressure, at elevated temperature, and/or in the presence of a penetration enhancer, such as dimethylsulfoxide.

Other methods of introducing at least one radiosensitizer into a polymeric material include, but are not limited to, the following: applying a gas containing the radiosensitizer(s), under pressure and/or at elevated temperature; injecting the radiosensitizer(s) or a solution containing the radiosensitizer(s) directly into the polymeric material; placing the polymeric material under reduced pressure and then introducing a gas or solution containing the radiosensitizer(s); dehydrating the polymeric material, such as by using a buffer of high ionic and/or osmolar strength, and rehydrating the polymeric material with a solution containing the radiosensitizer(s); applying a high ionic strength solvent containing the radiosensitizer(s), which may optionally be followed by a controlled reduction in the ionic strength of the solvent; cycling the polymeric material between solutions of high ionic and/or osmolar strength and solutions of low ionic and/or osmolar strength containing the radiosensitizer(s); applying the at least one radiosensitizer within or as a component of a microemulsion; and combinations of two or more of these methods.

The mechanism of action of many of these compounds involves its binding to the nucleic acid (DNA/RNA) of the contaminating microbe. Upon irradiation, the compound absorbs the energy and locally causes damage to the nucleic acid, thereby preventing replication of the microorganism. Since the polymeric materials do not contain nucleic acid, little damage is caused by the radiosensitizer after irradiation. Advantageously, since many of the radiosensitizers are considered safe for blood product sterilization, their safety/toxicity profile is generally favorable and they can remain on a medical device with little risk to the patient.

The method disclosed herein is effective against such biological contaminants or pathogens, including the various viruses, bacteria (including inter- and intracellular bacteria, such as mycoplasmas, ureaplasmas, nanobacteria, chlamydia, rickettsias), yeasts and molds.

The radiation employed in the methods disclosed herein may be any radiation effective for the sterilization of the polymeric material being treated. The radiation may be corpuscular, including accelerated electron irradiation (E-beam) radiation. The radiation may be electromagnetic radiation, including x-rays, infrared, visible light, UV light and mixtures of various wavelengths of electromagnetic radiation. The radiation may be gamma radiation from a cobalt or other isotopic source or irradiation with X-rays.

According to the methods disclosed herein, the polymeric material is irradiated with the radiation at a dose effective for the sterilization of the polymeric material, while not producing an unacceptable level of damage to that material. Suitable doses of irradiation may vary depending upon the nature and characteristics of the particular polymeric material being irradiated, the particular form of radiation involved and/or the particular biological contaminants or pathogens being inactivated. Suitable doses of irradiation can be determined empirically by one skilled in the art. The dose of irradiation may be constant for the duration of the sterilization procedure. When this is impractical or otherwise not desired, a variable or discontinuous irradiation may be utilized.

According to the methods disclosed herein, the dose of irradiation may be optimized to produce the most advantageous combination of product recovery and time required to complete the operation. Advantageously, low (<3 kGy) doses may be utilized in the methods described herein to achieve such results. The dose of irradiation is selected to minimize structural damage to the polymeric material while still sterilizing the polymeric material.

According to one form, the dose of irradiation is not more than about 5.0 kGy, or between about 0.1 kGy and 3.0 kGy, or between about 0.1 kGy and 1.0 kGy, or between about 0.1 kGy and 0.5 kGy, or between about 0.1 kGy and 0.3 kGy.

According to the methods disclosed herein, the polymeric material to be sterilized is irradiated with a dose effective for the sterilization of the polymeric material. Suitable irradiation doses may vary depending upon the particular form of radiation involved and/or the nature and characteristics of the particular polymeric material being irradiated. As may be appreciated, suitable irradiation doses can be determined empirically by one skilled in the art.

In certain forms disclosed herein, when the polymeric material to be treated contains an aqueous or non-aqueous solvent, or a mixture of such solvents, at least one stabilizer is introduced according to any of the methods and techniques known and available to one skilled in the art, including soaking the polymeric material in a solution containing the stabilizer(s), preferably under pressure, at elevated temperature and/or in the presence of a penetration enhancer, such as dimethylsulfoxide, and more preferably, when the stabilizer(s) is a protein, at a high concentration. Other methods of introducing at least one stabilizer into a polymeric material include, but are not limited to, the following: applying a gas containing the stabilizer(s), preferably under pressure and/or at elevated temperature; injecting the stabilizer(s) or a solution containing the stabilizer(s) directly into the polymeric material; placing the polymeric material under reduced pressure and then introducing a gas or solution containing the stabilizer(s); dehydrating the polymeric material, such as by using a buffer of high ionic and/or osmolar strength, and rehydrating the polymeric material with a solution containing the stabilizer(s); applying a high ionic strength solvent containing the stabilizer(s), which may optionally be followed by a controlled reduction in the ionic strength of the solvent; cycling the polymeric material between solutions of high ionic and/or osmolar strength and solutions of low ionic and/or osmolar strength containing the stabilizer(s); applying the at least one stabilizer within or as a component of a microemulsion; and combinations of two or more of these methods.

In certain forms disclosed herein, at least one cryopreservative is introduced into a polymeric material according to any of the methods and techniques known and available to one skilled in the art, including soaking the polymeric material in a solution containing the cryopreservative(s), preferably under pressure, at elevated temperature and/or in the presence of a penetration enhancer, such as dimethylsulfoxide. Other methods of introducing at least one cryopreservative into a polymeric material include, but are not limited to, the following: applying a gas containing the cryopreservative(s), under pressure and/or at elevated temperature; injecting the cryopreservative(s) or a solution containing the cryopreservative(s) directly into the polymeric material; placing the polymeric material under reduced pressure and then introducing a gas or solution containing the cryopreservative(s); dehydrating the polymeric material, such as by using a buffer of high ionic and/or osmolar strength, and rehydrating the polymeric material with a solution containing the cryopreservative(s); applying a high ionic strength solvent containing the cryopreservative(s), which may optionally be followed by a controlled reduction in the ionic strength of the solvent; cycling the polymeric material between solutions of high ionic and/or osmolar strength and solutions of low ionic and/or osmolar strength containing the cryopreservative(s); applying the at least one cryopreservative within or as a component of a microemulsion; and combinations of two or more of these methods.

According to certain forms disclosed herein, the polymeric material may be subjected to a treatment effective to enhance penetration of the one or more stabilizers and/or cryopreservatives and/or sensitizers into the polymeric material. Such treatments include physical treatments and chemical treatments.

For instance, with respect to chemical treatment, the polymeric material may be treated with one or more compounds that cause an increase in the distance between molecules in the polymeric material, thereby promoting penetration of the stabilizers and/or cryopreservatives and/or sensitizers into the polymeric material. Alternatively, the chemical treatment may include treating the polymeric material with a microemulsion effective to enhance penetration of the stabilizers and/or cryopreservatives and/or sensitizers into the polymeric material.

Similarly, the polymeric material may be treated with one or more compounds that cause macromolecules in the polymeric material to become less compact, or relaxed, thereby promoting penetration of the stabilizer(s) and/or cryopreservatives and/or sensitizer(s) into the polymeric material or providing a greater surface area of polymeric material to be in contact with the stabilizer(s) and/or cryopreservatives and/or sensitizer(s). The compounds that cause macromolecules in the polymeric material to become less compact, or relaxed, may also be applied prior to introduction of the stabilizer(s) and/or cryopreservatives and/or sensitizer(s), which may then be introduced in a similar solution followed by application of a solution containing a similar amount of stabilizer(s) and/or cryopreservatives and/or sensitizer(s) but a reduced amount of the compounds that cause macromolecules in the polymeric material to become less compact, or relaxed. Repeated applications of such solutions, with progressively lower amounts of compounds that cause macromolecules in the polymeric material to become less compact, or relaxed, may subsequently he applied.

The compounds that promote penetration may be used alone or in combination, such as a combination of a compound that causes macromolecules in the polymeric material to become less compact and a compound that causes an increase in the distance between molecules in the polymeric material.

Further, in those forms wherein the stabilizer(s) and/or cryopreservatives and/or sensitizer(s) is cationic, one or more anionic compounds may be added to the solution containing the stabilizer(s) and/or cryopreservatives and/or sensitizer(s) prior to and/or during application thereof to the polymeric material. The anionic compound(s) may also be applied prior to introduction of the stabilizer(s) and/or cryopreservatives and/or sensitizer(s), which may then be introduced in a similar solution followed by application of a solution containing a similar amount of stabilizer(s) and/or cryopreservatives and/or sensitizer(s) but a reduced amount of the anionic compound(s). Repeated applications of such solutions, with progressively lower amounts of anionic compound(s) may subsequently be applied.

Similarly, in those forms wherein the stabilizer(s) and/or cryopreservatives and/or sensitizer(s) are anionic, one or more cationic compounds may be added to the solution containing the stabilizer(s) and/or cryopreservatives and/or sensitizer(s) prior to and/or during application thereof to the polymeric material. The cationic compound(s) may also be applied prior to introduction of the stabilizer(s) and/or cryopreservatives and/or sensitizer(s), which may then be introduced in a similar solution followed by application of a solution containing a similar amount of stabilizer(s) and/or cryopreservatives and/or sensitizer(s) but a reduced amount of the cationic compound(s). Repeated applications of such solutions, with progressively lower amounts of cationic compound(s) may subsequently be applied.

Regarding physical treatments effective to enhance penetration of the one or more stabilizer(s) and/or cryopreservative(s) and/or sensitizer(s) into the polymeric material, examples include, but are not limited to, physical agitation, such as by shaking or sonication.

According to the forms employing physical agitation, such as sonication or shaking, physical agitation is carried out for a time effective to enhance penetration of the one or more stabilizer(s) and/or cryopreservative(s) and/or sensitizer(s) into the polymeric material. The duration of such treatment will depend upon, among other factors, the nature of the one or more polymeric material, the nature of the solvent(s) employed, and the nature of the one or more stabilizer(s) and/or cryopreservative(s) and/or sensitizer(s). Suitable times may easily be determined empirically by one having ordinary skill in the art.

Polymers contemplated for use in the medical devices and articles disclosed herein include, but are not limited to, bioabsorbable polymers such as poly(lactide), including L (−), D (+), meso and racemic lactide form, poly(glycolide), poly (dioxanone), poly(ε-caprolactone), poly(hydroxybutyrate), poly(β-hydroxybutyrate), poly(hydroxyvalerate), poly(tetramethyl carbonate), and poly(amino acids) and copolymers and terpolymers thereof. Also contemplated herein is a copolymer blend comprising poly(lactide)-co-poly(glycolide) in a 50/50 wt. % ratio having a first copolymer of a weight average molecular weight between about 40,000 to about 100,000 Daltons, and a second copolymer of a weight average molecular weight between about 5,000 to about 30,000 Daltons.

As indicated above, contemplated for use herein is polylactic acid (PLA or poly(lactide)), which is prepared from the cyclic diester of lactic acid (lactide) by ring opening polymerization. As may be appreciated, lactic acid exists as two optical isomers or enantiomers. The L-enantiomer occurs in nature, a D, L racemic mixture results from the synthetic preparation of lactic acid. Fibers spun from "L" poly(lactide) (mp. 170 C) have high crystallinity, when drawn, whereas fibers spun from poly DL-lactide are amorphous. Crystalline poly-L-lactide is more resistant to hydrolytic degradation than the amorphous DL form.

High molecular weight PLA polymer can be readily prepared, with fiber samples having high tensile strength commercially available and produced by hot-drawing filaments spun from solution. Exposure of polylactic acid to gamma radiation has been shown to result in a decrease in molecular weight.

Unlike PLA, which is absorbed slowly, PGA is absorbed within a few months post-implantation, due to greater hydrolytic susceptibility. In vitro experiments have shown an effect on degradation by enzymes, buffer, pH, annealing treatments, and gamma irradiation. Acceleration of in vivo degradation due to gamma irradiation has been exploited to create devices where early fragmentation is desired. Polyglycolic acid (PGA or poly(glycolide)) is a totally synthetic absorbable polymer contemplated for use herein.

Also contemplated for use herein are copolymers of PGA and PLA, namely poly(lactide-co-glycolide). The copolymers are amorphous between the compositional range 25 to 70 mole percent glycolide. Pure polyglycolide is about 50% crystalline, whereas pure poly-L-lactide is reported to be about 37% crystalline. Like pure PGA and pure PLA, a 90/10 PGA/PLA is also weakened by gamma irradiation. Another approach to copolymerization includes using a starting monomer that is neither lactide nor glycolide, but rather an unsymmetrical cyclic diester containing one lactate and one glycolate moiety. This monomer produces a polymer with the same empirical formula as poly(lactide-co-50%-glycolide), but possesses different properties due to a more stereoregular configuration.

Another polymer contemplated for use herein is polydioxanone. The monomer p-dioxanone, is analogous to glycolide but yields a poly-(ether-ester). Poly(dioxanone) monofilament fibers are known to retain tensile strength longer than braided polyglycolide and are absorbed within about six months with minimal tissue response. Poly(dioxanone) degradation in vitro is affected by gamma irradiation dosage, but not substantially by the presence of enzymes.

Also contemplated for use herein is the polymer poly(ε-caprolactone). Poly(ε-caprolactone) is synthesized from ε-caprolactone. Additionally, copolymers of ε-caprolactone and L-lactide are contemplated for use herein. They are known to be elastomeric when prepared from 25% ε-caprolactone, 75% L-lactide and rigid when prepared from 10% ε-caprolactone, 90% L-lactide.

Also contemplated for use herein are the bioabsorbable polymers poly(hydroxybutyrate) and poly(hydroxyvalerate).

Poly(β-hydroxybutyrate) (PHB) is a biodegradable polymer that occurs both in nature and can easily be synthesized in vitro. Synthetic PHB, however, has not shown the stereoregularity found in the natural product. High MW, crystalline, and optically active PHB have been extracted from bacteria. PHB polymer is melt processable and has been proposed for use as absorbable suture. Recent improvements in the extraction process have resulted in renewed interest in PHB for both medical and nonmedical applications. Copolymers of hydroxybutyrate and hydroxyvalerate have been developed to provide a wide variety of mechanical properties and more rapid degradation than can be achieved with pure PHB, and are also contemplated for use herein.

Also potentially benefiting from the methods disclosed herein is the class of absorbable polymers known as poly (amino acids). The use of amino acids as building blocks for synthetic absorbable polymers has made great strides.

Also contemplated for use herein are the bioabsorbable polymers categorized as proteinaceous polymers. Such polymers include, without limitation, alginate albumins, algal proteins, apoproteins, lectins, lipoproteins, metalloproteins, polyproteins, collagen, elastin, fibronectins, laminin, tenascin, vitronectin, fibroin, gelatin, keratin, reticulin, poly(alpha-amino acid), poly(beta-amino acid), poly(gamma-amino acid), polyimino acid, polypeptide and derivatives of any of the above. As will be shown in more detail below, the proteinaceous polymer may comprise gelatin.

Also contemplated for use herein are nonabsorbable polymers, including, but not limited to, polyolefins, polycarbonates, polyvinylchlorides, styrenes, including acrylonitrile butadiene styrenes, nylons, acrylics, thermoplastic urethanes, thermoplastic elastomers, thermoset plastics, polyamides, polyesters and polyethylene terephthalate. Examples of polyolefins for use herein include, but are not limited to alpha-olefins produced by Ziegler-Natta or metallocene catalysts, such as polyethylene, polypropylene, copolymers and terpolymers thereof.

Medical devices produced in accordance herewith are not believed to suffer physical or mechanical damage during sterilization, when such sterilization is conducted in accordance with the methods disclosed herein. In production of the medical devices disclosed herein, the radiosensitizers could be coated onto the medical device or packaging material, injected into a package, or delivered in some other manner prior to irradiation. The medical devices contemplated herein include those selected from the group consisting of sutures, clips, staples, pins, screws, fibers, films, stents, gelcaps, tablets, microspheres and injectable polymer solutions.

Specific embodiments of the present invention will now be described further, by way of example. While the following examples demonstrate certain embodiments of the invention, they are not to be interpreted as limiting the scope of the invention, but rather as contributing to a complete description of the invention.

EXAMPLES

Example 1

Radiosensitization of Bacteria Coated Onto a Material Surface

*Enterococcus faecalis* ATCC 29212, grown overnight in tryptic soy broth at 37° C. without shaking, were centrifuged and resuspended in 2% glucose at a concentration of about $5 \times 10^7$ cfu/ml. The radiosensitizer compounds listed below, riboflavin, methylene blue, ascorbic acid, sodium nitrate, and toluidine blue, were added to the bacteria at the concentrations indicated, then incubated for 2 hours at room temperature with shaking. The cfu contained in each sample were quantified by dilution plating and the values are listed as "post-treatment cfu added." None of the radiosensitizer treatments alone appeared to have a significant adverse effect on the bacteria.

Following radiosensitizer treatment, 0.05 ml of each mixture (containing approximately $1 \times 10^6$ cfu) was spotted onto sterile 12 mm paper disks and the disks air dried for 30 minutes. The disks were then placed in sterile tubes and left untreated or irradiated with 0.3 kGy. The cfu were recovered from the disks by vortexing with glass beads for 1 minute in 0.85% saline with 0.35 g/l lecithin and 2.5 ml/l Tween 80. Quantification of the cfu was then performed by dilution plating onto tryptic soy agar.

Compared to the non-irradiated samples, the percentage of cfu recovered from the irradiated radiosensitizer-treated samples was lower that that of the untreated control. Thus, the radiosensitizer treatment enhanced the killing efficiency of the irradiation, with methylene blue, ascorbic acid, toluidine blue and sodium nitrate having the greatest effect.

TABLE 1

| Treatment | Conc. (μg/ml) ml | Post-Treatment CFU Added | 0 kGy | 0.3 kGy | Percent Survival 0.3 vs. 0 kGy |
|---|---|---|---|---|---|
| Control | | 9.00E+05 | 990 | 51 | 5.15 |
| Riboflavin | 200 | 8.50E+05 | 1080 | 3 | 0.28 |
| | 1000 | 8.00E+05 | 1080 | 9 | 0.83 |
| Methylene Blue | 20 | 7.80E+05 | 2250 | 3 | 0.13 |
| Ascorbic Acid | 200 | 8.55E+05 | 3270 | 9 | 0.28 |
| Sodium Nitrate | 5000 | 8.15E+05 | 420 | 0 | 0.00 |
| Toluidine Blue | 20 | 7.70E+05 | 87 | 0 | 0.00 |
| | 100 | 4.65E+05 | 72 | 0 | 0.00 |

Example 2

Radiosensitization of Bacteria Coated onto a Medical Device Comprised of Synthetic Polymer

*Enterococcus faecalis* ATCC 29212, grown overnight in tryptic soy broth at 37° C. without shaking, were centrifuged and resuspended in phosphate buffered saline (PBS) at a concentration of roughly $2 \times 10^9$ cfu/ml. The bacteria were then incubated for 2 hours at room temperature with or without 50 μg/ml methylene blue. The cfu contained in each sample after this incubation were quantified by dilution plating. The untreated sample contained $1.8 \times 10^9$ cfu/ml and the sample treated with methylene blue contained $1.6 \times 10^9$ cfu/ml, indicating that incubation with methylene blue did not significantly affect the bacterial number.

Following radiosensitizer treatment, 0.01 ml of each mixture (containing approximately $2 \times 10^7$ cfu) was spotted onto nine 1 cm×1 cm squares of Vicryl® mesh that were then air dried for 60 minutes. Triplicate samples were then placed in sterile tubes and left untreated or irradiated with 0.1 or 0.2 kGy. The cfu were recovered from the meshes by vortexing with glass beads for 1 minute in 0.85% saline with 0.35 g/l lecithin and 2.5 ml/l Tween 80. Quantification of the cfu was then performed by dilution plating onto tryptic soy agar.

TABLE 2

| | kGy | Inoculum | Plated CFU | Total CFU Rec | Avg CFU Rec | Std Dev | Log Total CFU | Avg Log CFU | Std Dev Log |
|---|---|---|---|---|---|---|---|---|---|
| Control | 0 | 1.80E+07 | 8.80E+05 | 4.40E+06 | 2.70E+06 | 1.68E+06 | 6.64 | 6.36 | 0.32 |
| | | | 5.30E+05 | 2.65E+06 | | | 6.42 | | |
| | | | 2.10E+05 | 1.05E+06 | | | 6.02 | | |
| | 0.1 | | 6.10E+04 | 3.05E+05 | 3.85E+05 | 7.09E+04 | 5.48 | 5.58 | 0.08 |
| | | | 8.80E+04 | 4.40E+05 | | | 5.641 | | |
| | | | 8.20E+04 | 4.10E+05 | | | 5.61 | | |
| | 0.2 | | 1.05E+04 | 5.25E+04 | 8.00E+04 | 4.05E+04 | 4.72 | 4.87 | 0.20 |
| | | | 2.53E+04 | 1.27E+05 | | | 5.10 | | |
| | | | 1.22E+04 | 6.10E+04 | | | 4.79 | | |
| 50 μg/l MB | 0 | 1.60E+07 | 2.33E+05 | 1.17E+06 | 7.40E+05 | 5.38E+05 | 6.07 | 5.72 | 0.51 |
| | | | 1.84E+05 | 9.20E+05 | | | 5.96 | | |
| | | | 2.70E+04 | 1.35E+05 | | | 5.13 | | |
| | 0.1 | | 7.60E+02 | 3.80E+03 | 1.04E+04 | 9.28E+03 | 3.58 | 3.90 | 0.38 |
| | | | 4.20E+03 | 2.10E+04 | | | 4.32 | | |
| | | | 1.27E+03 | 6.35E+03 | | | 3.80 | | |
| | 0.2 | | 5.20E+02 | 2.60E+03 | 1.83E+03 | 1.37E+03 | 3.41 | 3.08 | 0.59 |
| | | | 5.30E+02 | 2.65E+03 | | | 3.42 | | |
| | | | 5.00E+01 | 2.50E+02 | | | 2.40 | | |

Figure 2:
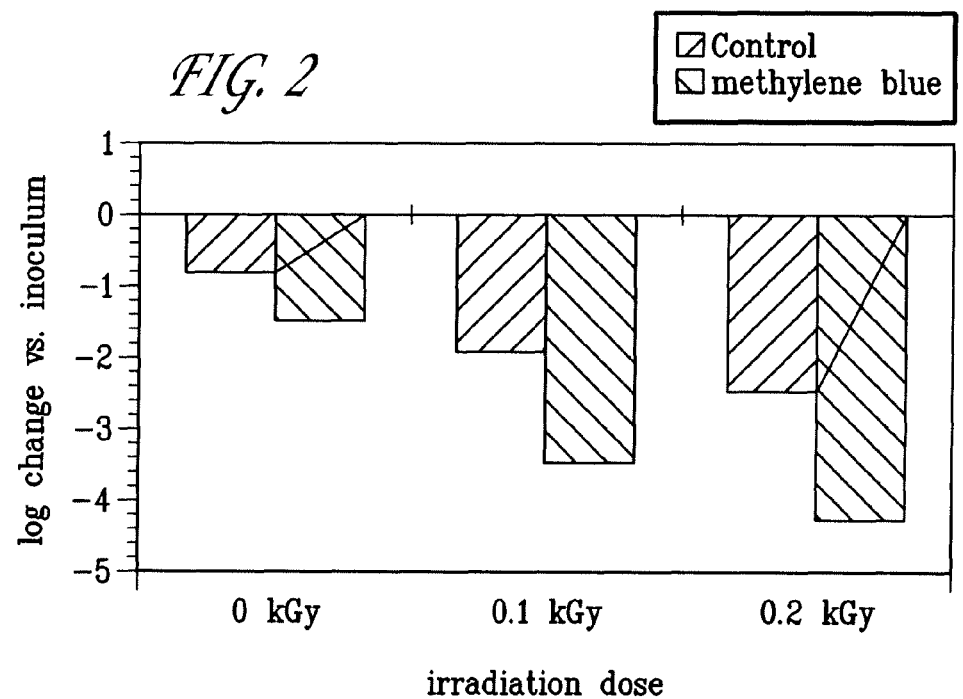
FIG. 2 presents plots of log change vs. inoculum as a function of irradiation dose for the data of Table 2.

FIG. 1 presents plots of cfu recovered as a function of irradiation dose for the data of Table 2. FIG. 2 presents plots of log change vs. inoculum as a function of irradiation dose for the data of Table 2. As may be seen, a 15% recovery from the control, unirradiated sample was observed. A 4.6% recovery from the methylene blue-treated, unirradiated sample was observed. Also, it may be noted that methylene blue had a small effect on bacterial recovery in this experiment. A 0.1 kGy dose caused a 0.8-log reduction in the untreated control, while a 0.2 kGy dose caused a 1.5-log reduction in the untreated control. The combination of methylene blue and a 0.1 dose or a 0.2 kGy dose caused a 3 to 4 log reduction in cfu recovered.

Example 3

Radiosensitization of Bacteria Coated onto a Medical Device Comprised of Prolene® and Vicryl® Synthetic Polymers

*Enterococcus faecalis* ATCC 29212, grown overnight in tryptic soy broth at 37° C. without shaking, were centrifuged and resuspended in phosphate buffered saline (PBS) at a concentration of about $5 \times 10^8$ cfu/ml. The bacteria were then incubated for 2 hours at room temperature with or without 50 µg/ml methylene blue. The cfu contained in each sample after this incubation were quantified by dilution plating. The untreated sample contained $4.8 \times 10^8$ cfu/ml and the sample treated with methylene blue contained $4.2 \times 10^8$ cfu/ml, indicating that incubation with methylene blue did not significantly affect the bacterial number.

Following radiosensitizer treatment, 0.01 ml of each mixture (containing approximately $5 \times 10^8$ cfu) was spotted onto nine 1 cm×1 cm squares of Prolene® mesh that were then air dried for 60 minutes. Triplicate samples were then placed in sterile tubes and left untreated or irradiated with 0.1 or 0.3 kGy. The cfu were recovered from the mesh by vortexing with glass beads for 1 minute in 0.85% saline with 0.35 g/l lecithin and 2.5 ml/l Tween 80. Quantification of the cfu was then performed by dilution plating onto tryptic soy agar.

TABLE 3

Test Results for Prolene ® Samples

|  | kGy | Inoculum | Plated CFU | Total CFU Recovered | Avg CFU Recovered | Std Dev | Log Red v Inoculum | Log Red v 0 kGy | Log Red v Control |
|---|---|---|---|---|---|---|---|---|---|
| Control | 0.0 | 4.80E+06 | 4.60E+04 | 1.15E+05 | 8.33E+04 | 3.25E+04 | −1.8 | 0.0 | 0.0 |
|  |  |  | 2.00E+04 | 5.00E+04 |  |  |  |  |  |
|  |  |  | 3.40E+04 | 8.50E+04 |  |  |  |  |  |
|  | 0.3 |  | 4.00E+00 | 1.00E+01 | 1.50E+01 | 4.33E+00 | −5.5 | −3.7 | 0.0 |
|  |  |  | 7.00E+00 | 1.75E+01 |  |  |  |  |  |
|  |  |  | 7.00E+00 | 1.75E+01 |  |  |  |  |  |
| 50 µg/ml MethyleneBlue | 0.0 | 4.20E+06 | 5.90E+02 | 1.48E+03 | 2.38E+03 | 1.49E+03 | −3.2 | 0.0 | −1.5 |
|  |  |  | 6.20E+02 | 1.55E+03 |  |  |  |  |  |
|  |  |  | 1.64E+02 | 4.10E+03 |  |  |  |  |  |
|  | 0.3 |  | 0.00E+00 | 0.00E+00 | 0.00E+00 | 0.00E+00 | −6.6 | −3.4 | −1.2 |
|  |  |  | 0.00E+00 | 0.00E+00 |  |  |  |  |  |
|  |  |  | 0.00E+00 | 0.00E+00 |  |  |  |  |  |

Following radiosensitizer treatment, 0.01 ml of each mixture (containing approximately $5 \times 10^8$ cfu) was spotted onto nine 1 cm×1 cm squares of Vicryl® mesh that were then air dried for 60 minutes. Triplicate samples were then placed in sterile tubes and left untreated or irradiated with 0.1 or 0.3 kGy. The cfu were recovered from the mesh by vortexing with glass beads for 1 minute in 0.85% saline with 0.35 g/l lecithin and 2.5 ml/l Tween 80. Quantification of the cfu was then performed by dilution plating onto tryptic soy agar.

TABLE 4

Test Results for Vicryl ® Samples

|  | kGy | Inoculum | Plated CFU | Total CFU Recovered | Avg CFU Recovered | Std Dev | Log Red v Inoculum | Log Red v 0 kGy | Log Red v Control |
|---|---|---|---|---|---|---|---|---|---|
| Control | 0.0 | 4.80E+06 | 1.60E+04 | 4.00E+04 | 2.63E+05 | 2.30E+05 | −1.3 | 0.0 | 0.0 |
|  |  |  | 2.00E+05 | 5.00E+05 |  |  |  |  |  |
|  |  |  | 1.00E+05 | 2.50E+05 |  |  |  |  |  |
|  | 0.3 |  | 7.00E+02 | 1.75E+03 | 6.60E+02 | 9.49E+02 | −3.9 | −2.6 | 0.0 |
|  |  |  | 8.00E+00 | 2.00E+01 |  |  |  |  |  |
|  |  |  | 8.40E+01 | 2.10E+02 |  |  |  |  |  |
| 50 µg/ml MethyleneBlue | 0.0 | 4.20E+06 | 3.80E+03 | 9.50E+03 | 1.79E+04 | 8.14E+03 | −2.4 | 0.0 | −1.2 |
|  |  |  | 7.40E+03 | 1.85E+04 |  |  |  |  |  |
|  |  |  | 1.03E+02 | 2.58E+04 |  |  |  |  |  |
|  | 0.3 |  | 6.30E+01 | 1.58E+02 | 9.83E+01 | 8.57E+01 | −4.6 | −2.3 | −0.8 |
|  |  |  | 5.50E+01 | 1.38E+02 |  |  |  |  |  |
|  |  |  | 0.00E+00 | 0.00E+00 |  |  |  |  |  |

Figure 3:
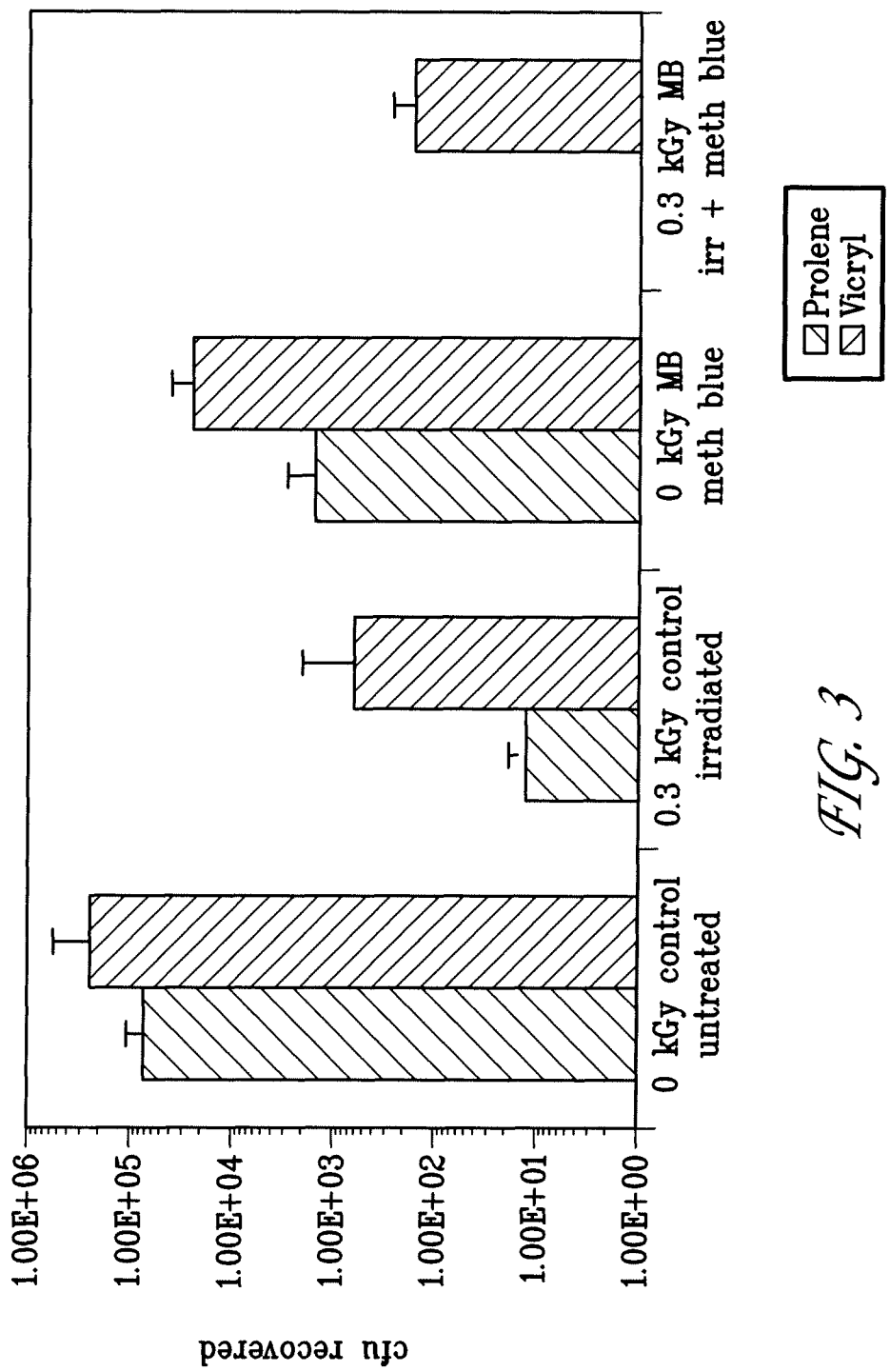
FIG. 3 presents plots of cfu recovered as a function of irradiation dose for the data of Tables 3 and 4.

FIG. 3 presents plots of cfu recovered as a function of irradiation dose for the data of Tables 3 and 4. As may be seen, the combination of methylene blue and irradiation significantly reduced the number of bacteria recovered from the Prolene® and Vicryl® mesh samples compared to methylene blue or irradiation alone. Methylene blue and gamma irradiation appear to act in a synergistic fashion to eliminate bacteria from the surface of the medical device, i.e. methylene blue enhanced the effect of irradiation in sterilization of the device.

Example 4

Radiosensitization of Bacteria Coated onto a Medical Device Comprised of Spongostan® Gelatin Sponge

*Enterococcus faecalis* ATCC 29212, grown overnight in tryptic soy broth at 37° C. without shaking, were centrifuged and resuspended in phosphate buffered saline (PBS) at a concentration of about $5 \times 10^8$ cfu/ml. The bacteria were then incubated for 2 hours at room temperature with 50 µg/ml methylene blue or with 2.5 mg/ml of riboflavin or without any further treatment. The cfu contained in each sample after this incubation were quantified by dilution plating. The untreated sample contained $4.8 \times 10^8$ cfu/ml, the sample treated with methylene blue contained $4.2 \times 10^8$ cfu/ml, indicating that incubation with methylene blue did not significantly affect the bacterial number and the sample treated with riboflavin also contained $4.2 \times 10^8$ cfu/ml, again indicating that incubation with riboflavin did not significantly affect the bacterial number Following radiosensitizer treatment, 0.01 ml of each mixture (containing approximately $5 \times 10^8$ cfu) was spotted onto nine 1 cm×1 cm squares of Spongostan® gelatin sponge that were then air dried for 60 minutes. (Spongostan® is a dry artificial sponge of fibrin prepared by clotting with thrombin, a foam or solution of fibrinogen. It is used in conjunction with thrombin as a hemostatic in surgery at sites where bleeding cannot be controlled by more common methods.) Triplicate samples were then placed in sterile tubes and left untreated or irradiated with 0.1 or 0.3 kGy. The cfu were recovered from the sponge by vortexing with glass beads for 1 minute in 0.85% saline with 0.35 g/l lecithin and 2.5 ml/l Tween 80. Quantification of the cfu was then performed by dilution plating onto tryptic soy agar.

Figure 4:
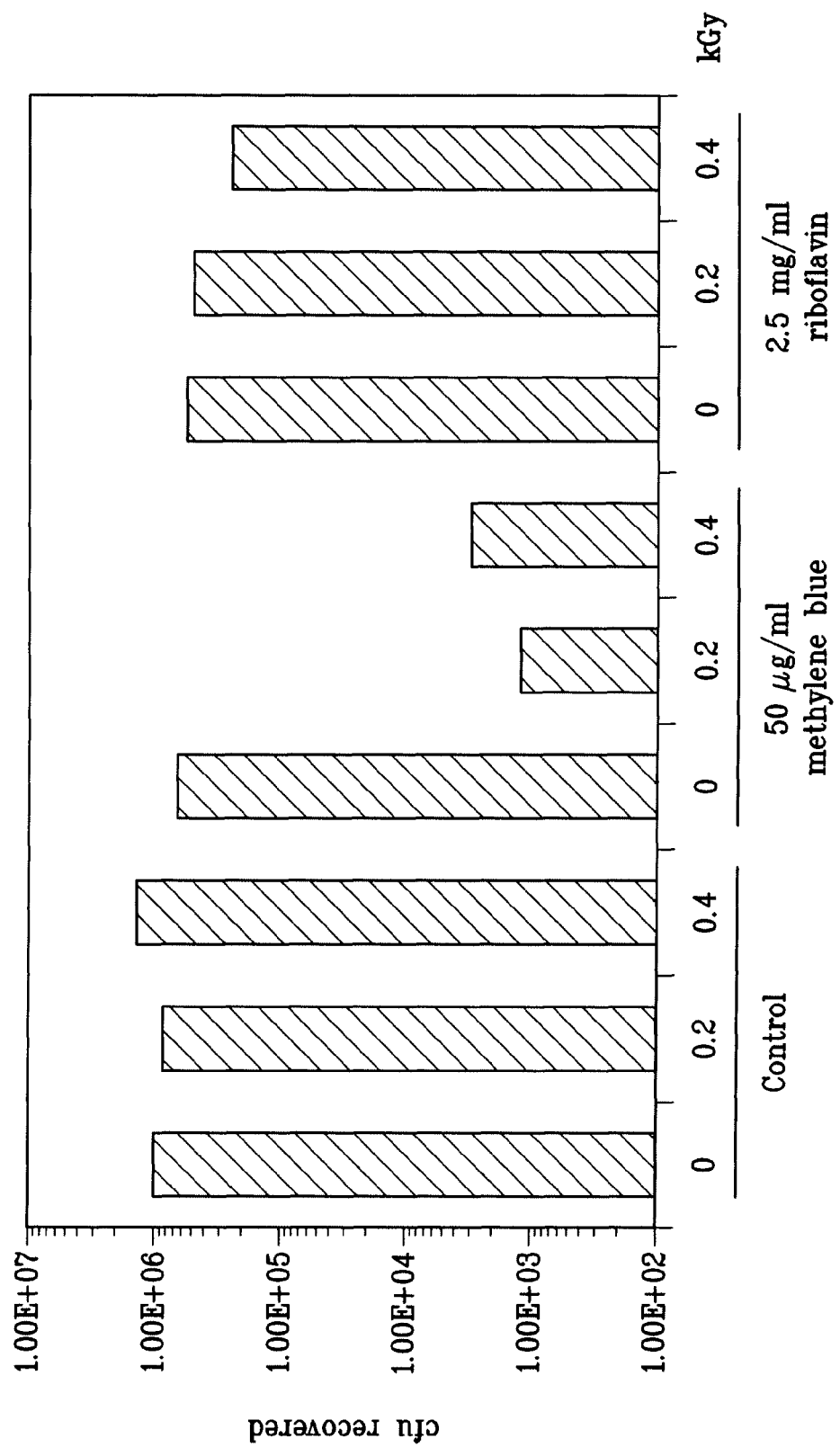
FIG. 4 presents plots of cfu recovered as a function of irradiation dose for the Spongostan® gelatin samples treated with 50 μg/ml methylene blue or with 2.5 mg/ml of riboflavin or left untreated as a control.
Figure 5:
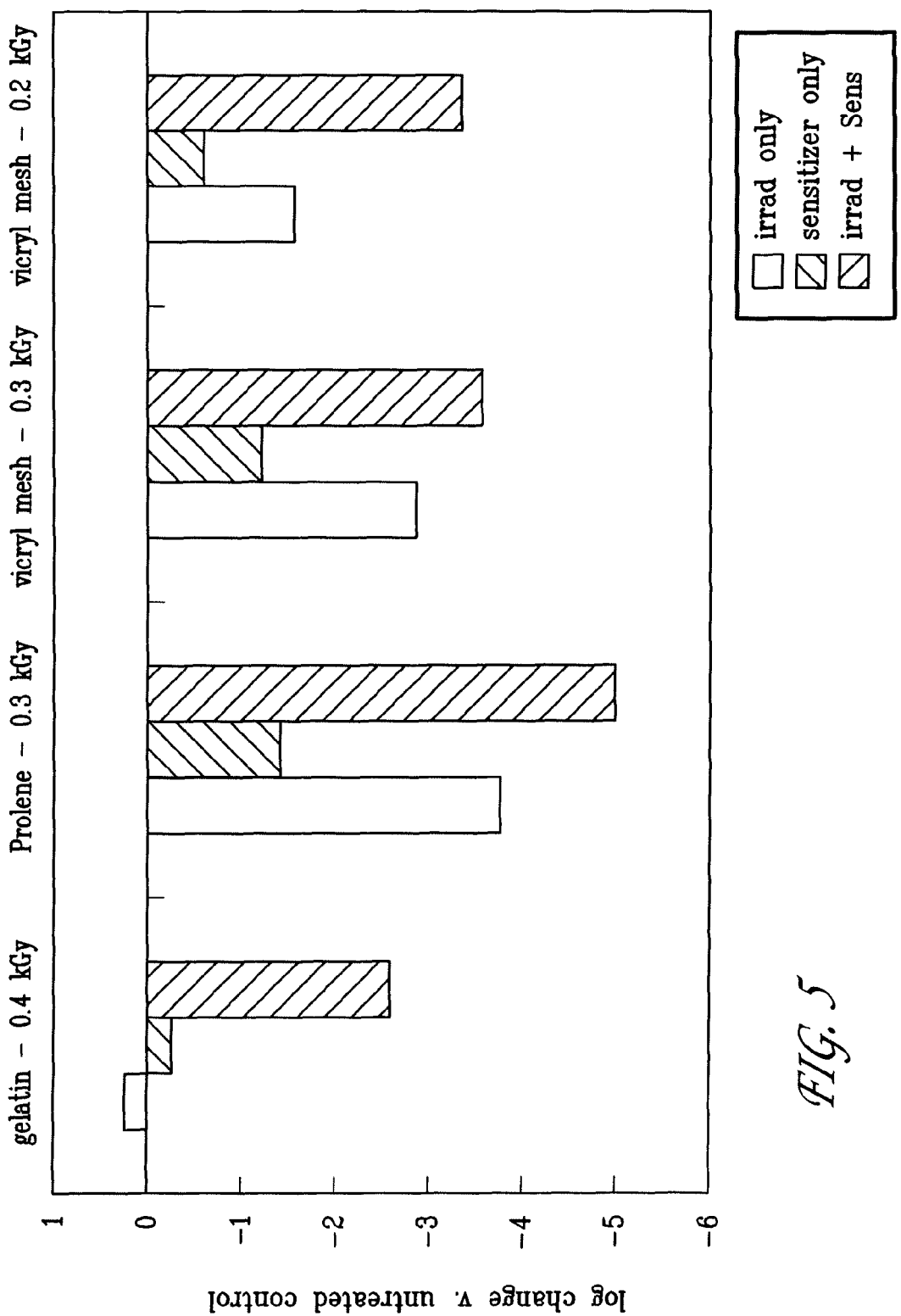
FIG. 5 presents a summary of the log change vs. untreated control as a function of irradiation dose for the data of Examples 1 through 4.

FIG. 4 presents plots of cfu recovered as a function of irradiation dose for the Spongostan® gelatin samples treated with 50 μg/ml methylene blue or with 2.5 mg/ml of riboflavin or left untreated as controls. FIG. 5 presents a summary of the log change vs. untreated control as a function of irradiation dose for the data of Examples 1 through 4.

As demonstrated hereinabove, the use of a radiosensitizer has been found to significantly reduce the dose of radiation used for disinfection, thereby ensuring that the structural features of the polymeric material are not significantly affected. The method disclosed herein provides a distinct advantage over currently used sterilization methods, such as ethylene oxide treatments, by reducing the cost, environmental impact, and processing time of sterilization of medical devices containing polymeric materials.

While the subject invention has been illustrated and described in detail in the drawings and foregoing description, the disclosed embodiments are illustrative and not restrictive in character. All changes and modifications that come within the scope of the invention are desired to be protected.

What is claimed is:

1. A method of making a polymeric medical device, comprising:
   (a) providing a bioabsorbable polymer composition;
   (b) heating the polymer to a melt processing temperature;
   (c) forming said medical device from the polymer composition using a melt processing apparatus, the medical device having at least a first surface;
   (d) applying at least one radiosensitizer to the at least first surface of the polymeric medical device; and
   (e) sterilizing said medical device with ionizing radiation selected from the group consisting of gamma radiation, E-beam radiation, x-ray radiation, and combinations thereof at a dose of between about 0.1 kGy and about 0.3 kGy;
   wherein the medical device is effective for its intended use following sterilization with radiation.

2. The method of claim 1, wherein the at least one radiosensitizer is selected from the group consisting of psoralen and its derivatives and analogs; inactines and their derivatives and analogs; angelicins; khellins; coumarins; nucleic acid binding compounds; brominated hematoporphyrin; phthalocyanines; purpurins; porphyrins; halogenated or metal atom-substituted derivatives of dihematoporphyrin esters, hematoporphyrin derivatives, benzoporphyrin derivatives, hydrodibenzoporphyrin dimaleimade, hydrodibenzoporphyrin, dicyano disulfone, tetracarbethoxy hydrodibenzoporphyrin, and tetracarbethoxy hydrodibenzoporphyrin dipropionamide; doxorubicin; daunomycin; netropsin; BD peptide, S2 peptide; S-303 (ALE compound); hypericin, methylene blue, toluidine blue, eosin, fluoresceins, flavins, merocyanine 540; bergapten; and SE peptide.

3. The method of claim 1, wherein the at least one radiosensitizer is methylene blue present in an amount of from about 20 μg/mL to about 75 μg/mL.

4. The method of claim 1, wherein the at least one radiosensitizer is riboflavin present in an amount of from about 200 μg/mL to about 5 mg/mL.

5. The method of claim 1, wherein the polymeric material comprises a polymer selected from the group consisting of poly(lactide), poly(glycolide), poly(dioxanone), poly(ε-caprolactone), poly(hydroxybutyrate), poly(β-hydroxybutyrate), poly(hydroxyvalerate), poly(tetramethyl carbonate), poly(lactide-co-glycolide), poly(amino acids) and copolymers and terpolymers thereof.

6. The method of claim 1, wherein the polymeric material comprises a proteinaceous polymer selected from the group consisting of alginate, albumins, algal proteins, apoproteins, lectins, lipoproteins, metalloproteins, polyproteins, collagen, elastin, fibronectins, laminin, tenascin, vitronectin, fibroin, gelatin, keratin, reticulin, poly(alpha-amino acid), poly(beta-amino acid), poly(gamma-amino acid), polyimino acid, polypeptide and derivatives thereof.

7. The method of claim 1, wherein the radiosensitizer is methylene blue and the polymeric material comprises gelatin.

8. The method of claim 1, wherein the radiosensitizer is riboflavin and the polymeric material comprises gelatin.

* * * * *